(12) United States Patent
Timko et al.

(10) Patent No.: US 6,649,746 B1
(45) Date of Patent: Nov. 18, 2003

(54) BIOLOGICAL PRODUCTION OF STABLE GLUTAMINE, POLY-GLUTAMINE DERIVATIVES IN TRANSGENIC ORGANISMS AND THEIR USE FOR THERAPEUTIC PURPOSES

(75) Inventors: Michael P. Timko, Charlottesville, VA (US); Richard L. Guerrant, Charlottesville, VA (US)

(73) Assignee: University of Virginia Patent Foundation, Charlottesville, VA (US)

(*) Notice: Subject to any disclaimer, the term of this patent is extended or adjusted under 35 U.S.C. 154(b) by 0 days.

(21) Appl. No.: 09/563,096

(22) Filed: May 2, 2000

Related U.S. Application Data
(60) Provisional application No. 60/133,014, filed on May 7, 1999.

(51) Int. Cl.$^7$ .................. C07H 21/04; A61K 38/00; C07K 16/00; C12N 5/00
(52) U.S. Cl. ............ 536/23.5; 536/23.1; 536/23.6; 536/23.7; 530/300; 530/324; 530/325; 530/326; 530/327; 530/328; 530/329; 530/330; 435/325
(58) Field of Search ................. 530/324–330, 530/300; 536/23.1–24.5; 435/325

(56) References Cited

U.S. PATENT DOCUMENTS

| | | | |
|---|---|---|---|
| 4,101,536 A | 7/1978 | Yamamura et al. | 530/322 |
| 4,377,570 A | 3/1983 | Durette et al. | 424/88 |
| 4,474,754 A | 10/1984 | Shimizu et al. | 424/85 |
| 4,693,998 A | 9/1987 | Lefrancier et al. | 514/62 |
| 4,868,155 A | 9/1989 | Durette et al. | 514/19 |
| 4,898,879 A | 2/1990 | Madsen et al. | 514/400 |
| 4,975,374 A | 12/1990 | Goodman et al. | 435/172.3 |
| 4,987,123 A | 1/1991 | Masaki et al. | 514/19 |
| 5,032,675 A | 7/1991 | Kato et al. | 530/337 |
| 5,034,377 A | 7/1991 | Adibi et al. | 514/18 |
| 5,036,052 A | 7/1991 | Ozeki et al. | 514/19 |
| 5,098,838 A | 3/1992 | Goodman et al. | 435/183 |
| 5,189,016 A | 2/1993 | Madsen et al. | 514/2 |
| 5,276,018 A | 1/1994 | Wilmore | 514/23 |
| 5,290,757 A | 3/1994 | Christains et al. | 504/335 |
| 5,292,722 A | 3/1994 | Wilmore | 514/23 |
| 5,310,768 A | 5/1994 | Vinnars | 514/574 |
| 5,380,934 A | 1/1995 | Inoue et al. | 562/561 |
| 5,432,160 A | 7/1995 | Hara et al. | 514/19 |
| 5,534,538 A | 7/1996 | Drauz et al. | 514/19 |
| 5,543,397 A | 8/1996 | Druaz et al. | 514/19 |
| 5,550,283 A | 8/1996 | Inoue et al. | 562/561 |
| 5,559,092 A | 9/1996 | Gibson et al. | 514/2 |
| 5,561,111 A | 10/1996 | Guerrant et al. | 514/17 |
| 5,627,047 A | 5/1997 | Brenner et al. | 435/69.1 |
| 5,658,895 A | 8/1997 | Aoi et al. | 514/58 |
| 5,719,119 A | 2/1998 | Veech | 514/2 |
| 5,804,442 A | 9/1998 | Romet-Lemonne et al. | 435/374 |

FOREIGN PATENT DOCUMENTS

| | | |
|---|---|---|
| DE | 4231675 | 3/1994 |
| EP | 0082184 | 6/1983 |
| EP | 87750 | 9/1983 |
| EP | 0098520 | 1/1984 |
| EP | 220379 | 5/1987 |
| EP | 0250559 | 1/1988 |
| EP | 0311057 | 4/1989 |
| EP | 0318446 | 5/1989 |
| EP | 0398879 | 11/1990 |
| EP | 0457314 | 11/1991 |
| EP | 0571198 | 5/1993 |
| EP | 0560989 | 9/1993 |
| EP | 0634168 | 1/1995 |
| EP | 0649304 | 4/1995 |
| EP | 753064 | 1/1997 |
| EP | 625313 | 10/1998 |
| EP | 875155 | 11/1998 |
| FR | 2533827 | 4/1984 |
| JP | 6234715 | 8/1994 |
| JP | 8325131 | 12/1996 |
| WO | 9118010 | 11/1991 |
| WO | 9209277 | 6/1992 |
| WO | 9516039 | 6/1995 |
| WO | 9700081 | 1/1997 |
| WO | 9705890 | 2/1997 |
| WO | 9846251 | 10/1998 |

OTHER PUBLICATIONS (Rev. Hosp. Clin. Fac. Med. Sao Paulo (2002) 57(4): 187–198).*
(Curr Opin Clin Nutr Metab Care (1999) 2(4) 323–7).*
(Clinical Infectious Diseases (2000) 31(1):277).*
Hadasch et al. (Intervirology (1993) 36: 32–43).*

\* cited by examiner

*Primary Examiner*—Jeffrey Siew
*Assistant Examiner*—Alexander H. Spiegler
(74) *Attorney, Agent, or Firm*—John P. Breen

(57) ABSTRACT

The invention provides a bioproduction of glutamine rich peptides. These peptides are used for rehydration and nutrition therapy in patients and for enhanced nutrition in animals. The peptides may be used as individual peptides or combined with other peptides in oligopeptides or proteins. Compositions of glutamine rich peptides and nucleic acid sequences for producing such peptides, as well as methods of production and use, are described.

7 Claims, 1 Drawing Sheet

FIGURE 1

```
AGRP-1    MALQQAQQAQQKVQQDIQQPAQQAQQGQQVQQAQQDIQQTAQQAQQIQQRQQK

MET ALA LEU GLN GLN ALA GLN GLN ALA GLN GLN LYS VAL GLN GLN ASP
Oligo 1 C ATG GCT CTT CAA CAG GCA CAG CAG GCT CAA CAG AAA CTT CAG CAG GAT
Oligo 2       CGA GAA GTT GTC CGT GTC GTC CGA GTT GTC TTT GAA GTC GTC CTA TAG GTC ILE GLN GLN PRO ALA GLN GLN ALA GLN GLN GLY GLN GLN VAL GLN GLN ALA GLN GLN ASP
Oligo 3   ATC CAG CAA CCC GCT CAG CAG GCT CAA CAG GGT CAA CAG GTG CAG CAG GCT CAA CAG GAT
Oligo 4       GTT GGG CCA GTC GAC CGA GTT GTC CCA GTT GTC CAC GTC GTC CGA GTT GTC CTA TAG GTC ILE GLN GLN THR ALA GLN GLN ALA GLN GLN ILE GLN GLN ARG GLN GLN LYS ***
Oligo 5   ATC CAG CAA ACT GCT CAG CAG GCT CAA CAG ATA CAG CAG CGT CAA CAG AAA TAG GAT CCG AGC T
Oligo 6       GTT TGA CGA GTC GTC CGA GTT GAC TAT GTC GTC GCA GTT GTC TTT ATC CTA GGC
```

BIOLOGICAL PRODUCTION OF STABLE GLUTAMINE, POLY-GLUTAMINE DERIVATIVES IN TRANSGENIC ORGANISMS AND THEIR USE FOR THERAPEUTIC PURPOSES

This application claims the benefit of U.S. Provisional Application No. 60/133,014, filed May 7, 1999 herein incorporated by reference in its entirety.

BACKGROUND OF THE INVENTION

1. Field of Invention

The present invention relates to stable glutamine derivatives and their use in rehydration and nutrition therapy and for enhanced nutrition in animals. More particularly the present invention is directed to the bioproduction of polypeptides comprising glutamine or glutamine rich regions and use of these polypeptides for rehydration and nutrition therapy and enhanced nutrition in animals.

2. Background of Invention

Glutamine is an amino acid which cotransports $Na^+$ across the enterocyte brush border membrane. It is known to be the major bowel nutrient and energy source and has been used in intravenous solutions to improve nitrogen balance, inhibit protein breakdown, stimulate the growth of epithelial cells, and reduce intestinal villous atrophy. In addition, various researchers have shown that glutamine stimulates the absorption of sodium and chloride and have used glutamine in oral rehydration solutions to reduce cholera diarrhea.

Viral enteritis is a leading cause of diarrhea in infants and toddlers less than two years old. Each year in the United States, about 22,000 infants are hospitalized for treatment of rotavirus-induced dehydration. In a majority of the cases, diarrheal disease morbidity and mortality is due to dehydration. The primary effect seen is the loss of fluid and electrolytes in diarrheal stools. An immediate effect in treatment of dehydration can be achieved by early oral administration of sugar (glucose) and electrolyte solution and continued feeding. However, conventional therapy by administration of oral rehydration formulations does not reduce stool volume or the duration of diarrhea. Thus, modifications of the oral rehydration therapy are needed to actually reduce stool volumes or speed the recovery of normal mucosal function, which in term will substantially enhance the acceptability and effectiveness of such therapy. The effects of organic compounds of salt and water absorption were first applied successfully to the treatment of patients with chloera and thereafter it was shown experimentally that the salt substrate cotransport was substantially intact in cholera patients and that oral therapy with sodium, chloride, potassium, biocarbonate and glucose in the same solution will restore and maintain normal blood volume and electrolyte concentrations, organic molecules such as D-hexoses, neutral amino acids, dipeptides and tripeptides of neutral amino acids, and water soluble vitamins can also enhance sodium absorption, following by water absorption in the small intestines. The present inventors have previously shown the efficacy of glutamine in intestinal sodium absorption. (Lima et al., Brazilian J. Med. Biol Res., 25; 637–640, (1992)). However, the greatest limitations to the oral use of glutamine is its instability and tendency to degrade in water and acid, conditions which are found in the stomach.

Bone marrow transplantation is being increasingly used in the treatment of hematologic malignancies. Patients undergoing bone marrow transplantation loose body protein because of the catabolic of acts of chemotherapy, total body radiation and graft-versus host disease. In addition, gastrointestinal toxicity often limits the consumption absorption of enteral nutrients. Infectious complications also remain a major cause of morbidity of these patients. Infections accelerate protein loss, and protein-calories malnutrition may decrease host resistance to microbial invasion. Parenteral nutrition is known to attenuate such protein losses and may prevent complications associated with malnutrition. Despite use in many centers, parenteral nutrition is also, unfortunately, associated with an increased incidence of infection in patients receiving chemotherapy with or without the irradiation, and also in those receiving allogeneic bone marrow transplantation. Further, despite conventional nutritional support, these patients still suffer from markedly negative nitrogen balance.

Modification of amino acid formulation may improve the clinical and metabolic efficacy of parentenal nutrition. Notably absent in all commercially available parenteral nutrient solutions is glutamine, because it has a shorter shelf-life than the commonly used amino acids and has been considered a non-essential amino acid. However, during catabolic states, glutamine concentrations in intracelluar pools (primarily skeletal muscle) fall rapidly. This reduction in glutamine occurs due to use of glutamine for renal ammoniagenis and as oxidizable fuel for stimulated lymphocytes and macrophages and intestinal muscosal cells. Glutamine-enriched parenteral or enteral nutrition has been shown to enhance nitrogen balance, attenuate intestinal mucosal damage, decrease bactermia and improve survival after radiation and chemotherapy when compared with glutamine-free nutrition. Limited clinical studies in postoperative patients have shown improved nitrogen retention with glutamine-enriched parenteral feeding. The clinical safety of L-glutamine added as a component of balanced parenteral nutrient solutions has recently been documented (C. Ziegler et al., Annals of Internal Medicine, 116:821–828 (1992) and references cited therein incorporated herein by reference in its entirety).

In addition to the therapeutic value of L-glutamine in rehydration therapy and nutrition of diseased individuals, glutamine also has potential for a nutritional enhancement in healthy individuals. A stable glutamine derivative may form the basis for anabolic nutrient formulations for the building and sustaining of muscle mass in humans or other animals. For example these formulations may be desirable for use in connection with body building and athletic activities in humans and may be useful in optimizing feed rations for livestock.

While the efficacy of glutamine in rehydration and nutrition therapies and for nutritional enhancements is known, the instability of glutamine in the digestive tract has diminished its usefulness. Accordingly, there is a need for a method for administration of glutamine to humans or other animals which will provide effective treatment in oral rehydration and nutrition therapy or nutritional enhancements, while overcoming the difficulties of instability in acidic environment.

It has been previously reported that glutamine (GLN) and alanyl-glutamine (ALA-GLN) can be chemically synthesized and used to treat conditions associated with dehydration or nitrogen deficiency-based malnutrition. (See U.S. Pat. No. 5,561,111 to Guerrant et al. directed to Stable Glutamine Derivatives for Oral and Intravenous Rehydration and Therapy (ORNT) and U.S. patent application Ser. No. 09/527329 incorporated herein by reference in their entirety.) However, a biological production method could offer the advantages over chemical production methods in the preparation of glutamine rich peptides, oligopeptides and proteins for use in rehydration, and nutrition therapy and nutritional enhancement.

SUMMARY OF THE INVENTION

Accordingly, the present invention is directed to providing new stable glutamine derivatives capable of delivering glutamine to the body in oral or intravenous rehydration and nutrition therapy or in nutritional enhancement. In accordance with one embodiment of the invention the glutamine derivatives are expressed in a bacteria, yeast, plant or animal host cell that is part of a larger polypeptide. The proteins can be expressed under the control of a constitutive promoter or an inducible or developmentally regulated promoter. The expressed modified polypeptide can then be administered in either a purified form, an enriched formulation or in a non-purified form (i.e. administered in the cells in which the polypeptide was expressed) as an improved method for treating conditions associated with dehydration or nitrogen deficiency based malnutrition or as a nutritional supplement.

An objective of the present invention is a method for the bioengineered production of glutamine rich peptides which contain a principal component of glutamine (for example $(GLN)_n$ and $ALA(GLN)_n$) in one embodiment or in an alternative embodiment alanyl-glutamine $(ALA-GLN)_n$. These peptides may exist as peptides or be coupled with other like or different units to form oligopeptides, and/or proteins in prokaryotic or eukaryotic cells.

The method provides for the production of biologically relevant quantities of peptides, oligopeptides, and proteins containing one or more amino acid coupled with glutamine or polyglutamines tracts, with and without internal protease cleavage sites, by overexpression of DNA sequences encoding these peptides and the like in prokaryotic and eukaryotic cells including but not limited to bacteria (e.g., *Escherichia coli*, Pseudomonas sps., etc.), photosynthetic bacteria (e.g., Synechocystis sps. etc.), algae (e.g., Chlamydomonas, Chlorella, etc.), yeast (e.g., Saccharomyces sps.), plants (*Nicoliana tabacum, Zea mays, Glycine max*, etc.) and animal cells (e.g., BHK, 3T3) either cultured or as part of transgenic organisms, under the control of a constitutive promoter (i.e., gene transcription regulatory sequence(s)), an inducible or a developmentally-regulated promoter.

Additionally, the method provides for the bioengineered production of such GLN, ALA-GLN and GLN-rich peptides for example $(GLN)_n$, $ALA(GLN)_n$ and $(ALA-GLN)_n$, oligopeptides, and/or protein and the like, coupled to other existing cellular peptides or proteins which stabilize or enhance their formation or accumulation in the cell. The bioengineered peptides may be fused to another protein either at the C- or N-terminus. For example, this includes fusion to sequences for intracellular/intercellular localization (targeting sequences) and secretory sequences.

A further objective of the invention is to produce compositions of materials that result from the bioengineering process including nucleic acid molecules which code for at least one glutamine rich peptide, glutamine rich polypeptides produced by the bioengineering method, glutamine rich oligopeptides and glutamine rich proteins derivatives of glutamine rich polypeptides produced by the bioengineering method and the genetically modified strains of bacteria (e.g., *Escherichia coli*, Pseudomonas sps., etc.), photosynthetic bacteria (e.g., Synechocystis sps. etc.), algae (e.g., Chlamydononas, Chlorella, etc.), yeast (e.g., Saccharomyces sps.), plants (*Nicotiana tabacum, Zea mays, Glycine max*, etc.) and animals (e.g., BHK, 3T3), either cultured or as part of transgenic organisms, that express the proteins.

A further objective of the invention is a method for rehydration therapy comprising administering to a patent in need thereof an effective amount of biologically produced at least one glutamine rich peptide for example a peptide comprising the sequence of $(GLN)_n$, $(ALA-GLN)_n$ or $ALA(GLN)_n$. The biologically produced peptide may be a pure peptide, part of an oligopeptide comprised of like peptides, unlike peptides or a mixture thereof, or part of a protein comprised of like peptides, unlike peptides or a mixture thereof and may be administered in a purified form, and enriched formulation, or a non-purified form (i.e. administered in the cells or tissues in which the peptides, oligopeptides, or polypeptides are expressed).

A further objective of the invention is a method for nutrition therapy comprising administering to a patent in need thereof an effective amount of biologically produced at least one glutamine rich peptide for example a peptide comprising the sequence of $(GLN)_n$, $(ALA-GLN)_n$ or $ALA(GLN)_n$. The biologically produced peptide may be a pure peptide, part of an oligopeptide comprised of like peptides, unlike peptides or a mixture thereof, or part of a protein comprised of like peptides, unlike peptides or a mixture thereof and may be administered in a purified form, and enriched formulation or a non-purified form (e.g., administered in the cells or tissues in which the peptides, oligopeptides, or polypeptides are expressed).

A further objective of the invention is a method for building muscle mass in a healthy mammal comprising administering to an individual a biologically produced at least one glutamine rich peptide comprising for example a peptide comprising the sequence of $(GLN)_n$, $(ALA-GLN)_n$ or $ALA(GLN)_n$. The biologically produced peptide may be a pure peptide, part of an oligopeptide comprised of like peptides, unlike peptides or a mixture thereof, or part of a protein comprised of like peptides, unlike peptides or a mixture thereof and may be administered in a purified form, and enriched formulation or a non-purified form (i e. administered in the cells or tissues in which the peptides, oligopeptides, or polypeptides are expressed).

BRIEF DESCRIPTION OF THE FIGURES

FIG. 1 shows the DNA sequence which codes for an alanyl-glutamine rich species AGRP-1 (SEQ ID NO. 1) as well as the corresponding peptide sequence in accordance with an embodiment of the invention. The symbol *** is used in the figure to indicate that the corresponding codon (TAG) encodes a STOP or termination codon. Additionally, the nucleic acid sequence shown includes a sequence following the termination codon that provides a restriction site for cloning.

DETAILED DESCRIPTION OF THE INVENTION

The present invention is directed to compositions comprising bio-synthesized peptides, oligopeptides, proteins that have been modified to enhance their ALA-GLN and GLN content and use those proteins for oral or intravenous rehydration and nutrition therapy (ORNT). The invention produces by biological means GLN, ALA-GLN and GLN-rich peptides including but not limited to $(GLN)_n$, $ALA(GLN)_n$ and $(ALA-GLN)_n$, and derivatives suitable to serve as effective agents for oral and intravenous rehydration nutrition therapy ORNT and other applications.

These peptides may be used as individual peptides, linked to like peptides thereby forming of an oligopeptide or protein with repeating units of the peptide, or linked to unlike peptides to for other peptides, oligopeptides, or proteins, or linked to oligopeptides or proteins containing both like and unlike peptides. Additionally, the peptide may be linked to a protease cleavage site or a targeting signal.

The advantage of biological produced stabilized glutamine as part of $(GLN)_n$, $(ALA-GLN)_n$ or ALA $(GLN)_n$ peptides, oligopeptides and glutamine rich polypeptides over their chemical synthesis lies in the relative stability of the molecules. Glutamine is rapidly converted to Glutamic acid (GLU) in an acidic environment. As part of a peptide, oligopeptide or protein, the number of potential end chain target glutamines are limited and hence the glutamine available for oxidation is reduced. This makes administration of therapeutic amounts of the active peptide more efficient and effective.

In general, the feasibility of high level, cost-effective production of recombinant proteins and peptides in prokaryotic and eukaryotic cells has already been documented. (See Timko, M. P., Cahoon, A. B., Applied Plant Biotechnology, (V. L. Chopra, V. S. Malik, and S. R. Bhat eds.), Science Publishing Company, Enfield, N.H. (1999); and Molecular Biotechnology for Plant Food Production, (O. Paredes-Lopez, ed.), Technomic Publishing Company (1999) both incorporated herein by reference in their entirety.) Additionally, the use of glutamine and glutamine containing peptides as effective treatments for disease has been established. (See Lima et al., Cotransport of Sodium with Glutamine, Alanine and Glucose in the Isolated Rabbit Ileal Mucosa, Brazil. J. Med. Biol. Res. 25:637–640 (1992); Silva et al.; Efficacy of Glutamine-based Oral Rehydration Solution on Electrolyte and Water Absorption in Rabbit Model Secretory Diarrhea Induced by Cholera Toxin, J. Ped. Gastro. Nutri. 26:513–519 (1998) all incorporated herein by reference in their entirety.)

In describing the nucleic acid sequences of the present invention, both structure and function are utilized. The structure is provided by the above description of those nucleic acid sequences that encode peptide, oligopeptides or proteins having the same biological activity. Therefore, those nucleic acid sequences encoded and whose protein products have activity similar to that described above are included within the scope of the present invention. Additionally, those nucleic acid sequences encoding proteins to which these peptide fragments are adjoined are also included within the scope of the present invention.

As known to one skilled in the art, the symbol ALA is used to represent an abbreviation for alanine, the symbol GLN is the abbreviation for glutamine, and the symbol ALA-GLN is the dipeptide alanyl-glutamine. Additionally, in this description $ALA(GLN)_n$ designates a peptide having alanine in the terminal position and n glutamine units attached, while $(ALA-GLN)_n$ indicates a peptide composed of n alanyl-glutamine subunits and $(GLN)_n$ indicates a peptide composed of n glutamine subunits. Further, "n" notes the number of subunits units in the peptide. Peptides contain between about 1 and 20 subunits units (e.g. n is between about 1 and 20). As is well known to one knowledgeable in the art a peptide may be an independent species or a subunit of oligopeptide or protein.

In accordance with one embodiment of the invention, a peptide comprising a glutamine rich peptide for example $(GLN)_n$, $ALA(GLN)_n$, and/or $(ALA-GLN)_n$ is over expressed in a host cell. The host cell can be selected from the group consisting of prokaryotes and eukaryotes (including but not limited to bacteria, photosynthetic bacteria, algae, plant and animal cells). In one embodiment the protein is expressed in a host cell that is edible by a vertebrate species. For example, the proteins can be expressed in a plant crop species by transforming the plant species with the DNA sequence encoding the glutamine enriched peptide or protein. Thus, the nutritional value of the plant species is enhanced by the expression of the glutamine rich peptide, oligopeptide and/or protein encoded by the DNA of the transgenic plant gene sequence. In accordance with one embodiment of the invention, the nutritional value pet food, animal feed and forage crops can be enhanced by the expression of proteins in the present invention in forage/feed crops or other material used to generate animal feed/food.

The glutamine derivatives of the present invention can also be administered either in pure or substantially pure form. When administered orally, the contents can be administered as a liquid solution, powdered, tablet, capsule or lozenge. The compounds can be used in combination with one or more conventional pharmaceutical additives or excipients used in the preparations of tablets, capsules, lozenges and other orally administered forms. When administered as in intravenous solution, the derivatives of the present invention can be mixed with conventional IV solutions containing various amino acids and nutrients, such as conventional parenteral therapy solutions. Such IV solutions are known in the art and used in rehydration and nutrition therapy.

The compounds of the present invention are administered at a dose range effective to bring about improved intestinal sodium co-transport. A preferred dosage of glutamine equivalent for therapeutical purposes (GLN has a molecular weight of 145) is 0.05 to 0.8 g/kg/day of patient body weight, with approximately 0.5 to 0.6 g/kg/day or solutions of approximately 13 g/L glutamine equivalent (the solutions have sufficient glutamine derivative to provide an effective glutamine level equivalent to a solution of 13 g/L glutamine or 1–10 mM glutamine derivatives being most preferred.)

In accordance with one embodiment of the present invention native proteins are modified using techniques known to the skilled practitioner to enhance the protein content of glutamine or alanine/glutamine subunits. One method for accomplishing such a result is to modify the nucleic acid sequence of the peptide to substitute glutamine or alanyl glutamine, for the native amino acids. In accordance with one embodiment, additional nucleic acid sequence(s) can be added to nucleic acid sequences encoding the N-terminus or the C-terminus of the peptides or proteins. Nucleic acid sequences encoding for example a $(GLN)_n$, $ALA(GLN)_n$ or $(ALA-GLN)_n$ repeat can be inserted into the interior regions of the gene encoding the target protein. Furthermore, the method for producing the modified peptides, oligopeptides, and proteins of the present invention, having one or more amino acids with glutamine or polyglutamine attached thereto may also include internal protease cleavage sites that release the glutamine or alanine-glutamine repeat region upon contact with the protease, for example the use of trypin cleavage sites.

The invention is also directed to a method for making the bio-engineered peptides or oligopeptides and/or proteins, etc. in a biological expression system. This includes the process for biological synthesis of peptides such as $(GLN)_n$, $(ALA-GLN)_n$, and ALA $(GLN)_n$. Oligopeptides, or proteins with simple or complex repeats of this general pattern either by themselves or fused to another protein directed C-or N-terminus or in an internal region of the protein and with or without internal cleavage sites.

The present invention is also directed to the recombinant organisms including the plasmids, or relevant portions of the plasmid used for the production of the various bioengineered peptides, oligopeptides, and/or proteins, etc. This includes the process of generating the bioengineered peptides, oligopeptides, and/or proteins, and the like in transgenic organisms; the use of such organisms containing such nucleic sequences and their products for purposes including for rehydration and nutrition therapeutics and nutritional enhancements in healthy organisms.

Related to the bioengineering process: expression would be under the control of any suitable transcriptional control element in prokaryotic or eukaryotic cells and includes sequences for intracellular/intercellular localization (targeting sequences) and secretory sequences. Additionally the present invention is directed towards the use of biologically produced materials from recombinant organisms which have been bioengineered for the over production of GLN, ALA-GLN and the like based peptides, oligopeptides, and/or proteins, etc. in transgenic organisms including, but not limited to, bacteria, (for example *E.coli, Rhodohaacter capsulatus*), algae, (for example Chorella, Chlamydomonas), yeast, and plant (for example carrot, potato, corn, and banana) and animal cells. (See Timko, M. P., Cahoon, A. B., Applied Plant Biotechnology, (V. L. Chopra, V. S. Malik, and S. R. Bhat eds.), Science Publishing Company, Enfield, N.H. (1999) incorporated herein in its entirety by reference). These overproduced peptides, oligopeptides, and/or protein may be used directly by use of the cellular material of the transgenic organism or purified. These biologically-based synthesis methods for the chemical formation of $(GLN)_n$, $(ALA-GLN)_n$, and $ALA\,(GLN)_n$ peptides, oligopeptides, and/or proteins based on currently practiced recombinant DNA technologies have been developed for high yielding low cost source of poly-GLN and ALA-GLN peptides for use in glutamine-ORNT trials and therapies, other therapeutic uses and for nutritional enhancement in healthy mammals.

The combination of peptide overproduction in transgenic organisms for commercial purification and direct consumption offer distinct aggressive novel approach to the delivery of therapeutic or nutritional enhancement levels of glutamine or alanyl-glutamine to organisms.

The combination of peptide overproduction in transgenic organisms for commercial scale production and for direct consumption, offer distinct, aggressive novel approaches to the delivery of therapeutic levels of glutamine or alanyl-glutamine to patients and nutritional enhancement to healthy animals.

EXAMPLE 1

Design of the Putative Alanyl-glutamine Rich Repeat Protein (AGRP)

An example of the sequences that can be used are described below and typified by the sequence for AGRP-1. To address the generation of high levels of glutamine and/or alanyl-glutamine based peptides using a biological-based platform, one embodiment of the invention comprised designing a putative alanyl-glutamine rich repeat protein coding sequence (AGRP-1) by assembling a set of overlapping oligonucleotides (oligos) as shown in FIG. 1. The protein encoded by AGRP-1 (AGRP) contains approximately 50% glutamine residues of which all are amino-terminally blocked (e.g. by an ALA, LEU, ILE, GLY, VAL or ARG residue). The AGRP protein has a predicted molecular weight of approximately 6 kDa and has primarily α-helical structure. The stability of the protein in bacteria is predicted to be >30 hrs, allowing ample time for induction and recovery following expression. For expression in *E. coli* two different constructs have been generated. To assemble the putative AGRP-1 coding region, oligo 1 and 2 (SEQ ID NOS. 2 and 3); oligos 3 and 4 (SEQ ID NOS. 4 and 5); and oligos 4 and 5 (SEQ ID NOS. 6 and 7) were annealed at a 1:1 molar ratio by heating the mixture at 70° C. in 300 mM NaCl for 3 min and then slowly cool for about 1 hr. Prior to the annealing reaction, oligos 3 and 4 were phosphorylated with T4 polynucleotide kinase in the presence of excess ATP. The annealed 1/2 and 5/6 oligos were ligated to the ends of pBluescript vector linearized by digestion with NcoI and SacI using T4 ligase by incubation for 16 hr at 14° C. The ligation products were purified by electrophoresis through agarose gels. To the recovered modified vector, the annealed oligos 3/4 were ligated at ratios of vector to insert ranging from 1:1 to 1:5. The recovered circularized plasmids were transformed into *E coli* DH5α and selected on ampicillin containing LB plates. Random colonies were selected and the inserts sized and sequenced to recover the AGRP-1 containing sequences. Because of the possibility for concatemerization of 3/4, it was possible to recover protein coding regions of varying sizes. This embodiment of the invention work is directed to the minimal size shown above and in FIG. 1.

EXAMPLES 2–9

Other Examples of Bioengineered Peptides, Oligopeptides and/or Proteins

Other examples of types of bioengineered peptides, oligopeptides, and/or proteins, etc. that can be generated include but are not limited to the following, where the protein sequence is given by the three letter abbreviation of the amino acid (e.g., ALA=alanine; GLN=glutamine and the like, X=any amino acid) and the nucleic acid sequence is give by the one letter abbreviation for the base (e.g., A=adenine; G=guanine; C=cytosine; T=thymine; N=any of the four bases). Shown is the coding strand of the DNA. Note both amino acid sequence and nucleic acid sequence coding for the peptide sequence is provided.

EXAMPLE 2

ALA-GLN GCN-CAA/G (a) Repeats based on this dipeptide: [ALA-GLN]$_{(N)}$ [GCN-CAA/G]$_{(N)}$ (b) Repeats based on this dipeptide containing a starting Methionine residue:

MET-[ALA-GLN]$_{(N)}$     ATG-[GCN-CAA/G]$_{(N)}$

Resultant Peptides: ALA-GLN-ALA-GLN-ALA-GLA-ALA-GLN    (SEQ ID NO.8)

MET-ALA-GLN-ALA-GLN-ALA-GLA-ALA-GLN    (SEQ ID NO.9)

EXAMPLE 3

ALA-GLN$_{(N)}$ GCN-(CAA/G)$_{(N)}$ (a) Repeats based on this oligopeptide: [ALA-GLN$_{(N)}$]$_{(N)}$ [GCN-(CAA/G)$_{(N)}$]$_{(N)}$ (b) Repeats based on this dipeptide containing a starting Methionine residue:

MET-[ALA-GLN$_{(N)}$]$_{(N)}$ATG-[GCN-(CAA/G)$_{(N)}$]$_{(N)}$

```
Resultant Peptides: ALA-GLN-GLN-ALA-GLN-GLN-ALA-GLN-GLN-ALA-GLN-GLN      (SEQ ID NO.10);

ALA-GLN-GLN-GLN-ALA-GLN-GLN-GLN-ALA-GLN-GLN-GLN      (SEQ ID NO.11);

MET-ALA-GLN-GLN-ALA-GLN-GLN-ALA-GLN-GLN-ALA-GLN-GLN  (SEQ ID NO.12); and

MET-ALA-GLN-GLN-GLN-ALA-GLN-GLN-GLN-ALA-GLN-GLN-GLN  (SEQ ID NO.13).
```

EXAMPLE 4

Examples 2 or 3 in which the ALA has been substituted completely or randomly by another amino acid (designated X)

Resultant Peptides: ALA-[GLN$_{(N)}$]-LEU-[GLN$_{(N)}$]GCN-[(CAA/G)$_{(N)}$]-CTN-[(CAA/G)$_{(N)}$]MET-ALA-[GLN$_{(N)}$]-LEU-[GLN$_{(N)}$] ATG-GCN-[(CAA/G)$_{(N)}$]-CTN-[(CAA/G)$_{(N)}$]

EXAMPLE 5

Examples 2, 3, 4 in which the repeat units (i.e., ALA-GLN, ALA-GLN$_{(N)}$) are separated by amino acid residues constituting the target of a protease (defined below as a protease cleavage site) facilitating cleavage of the protein either in vivo or in vito.

MET- [ALA-GLN]$_{(N)}$-[protease cleavage site]-[ALA-GLN]$_{(N)}$

ATG-[GCN-CAA/G]$_{(N)}$-[protease cleavage site]-[GCN-CAA/G]$_{(N)}$ where the protease cleavage site is for example a trypsin cleavage site, chemotrypsin cleavage site, Factor Xa, r TEV cleavage site.

EXAMPLE 6

Examples 2, 3, 4, or 5 fused at their amino terminus or carboxy terminus to DNA sequences encoding amino acid residues capable of, but not limited to, serving as intracellular, intercellular, or secretory pathway targeting signals. An example of this is the chloroplast transit peptide signal sequences as described in the following patents and incorporated herein by reference in their entirety.

Chimaeric gene coding for a transit peptide and heterologous peptide. U.S. Pat. No. 5,717,084 to Herrera-Estrella, L., Van den Broeck, G., Van Montagu, M., Schreier, P. Schell, J., Bohnert, H. J., Cashmore, A. R., Timko, M. P., and Kausch, A. P.

Chimaeric gene coding for a transit peptide and heterologous polypeptide. U.S. Pat. No. 5,728,925. to Herrera-Estrella, L., Van den Broeck, G., Van Montagu, M., Schreier, P. Schell, J., Bohnert, H. J., Cashmore, A. R., Timko, M. P., and Kausch, A. P.

Another example is the apoplastic targeting signal.

EXAMPLE 7

Examples 2 through 6 fused at their amino terminus or carboxy terminus to DNA sequences encoding the amino acids of another unrelated peptide, oligopeptide or protein.

EXAMPLE 8

Materials based on Examples 2 through 7 made to provide any form of post-translational modification (glycosylation, phosphorylation, etc) and the resulting modified product.

EXAMPLE 9

Nucleic acid sequences identified in Examples 2–8 all contain a stop codon or termination signal encoded by the nucleotides TAA, TAG, TGA at their 3'-end.

EXAMPLE 10

Construction of Expression Vectors Containing the AGRP-1 and Related Coding Sequences Those of ordinary skill in the art will recognize that methods for vector construction and protein expression provided in the following examples are the preferred embodiment and that there are other techniques, vectors, and cell lines that could be implemented for constructing and expressing proteins or fragments thereof in either prokaryotic or eukaryotic systems. The preferred embodiment disclosed herein does not limit the scope of the invention, but rather is merely illustrative.

Methods which are well known to those skilled in the art can be used to construct expression vectors containing the nucleic acid sequences described above of which the AGRP-1 sequence is an example and appropriate transcriptional/translational control signals. These methods include but are not limited to in vitro recombinant DNA techniques, synthetic techniques and in vivo recombination/genetic recombination. See, for example, the techniques described in Maniatis et al., 1982 Molecular Cloning A Laboratory Manual, Cold Spring Harbor Laboratory, N.Y. incorporated herein by reference in its entirety.

A variety of host-expression vector systems may be utilized to express the AGRP-1 coding sequence. These include, but are not limited to, microorganisms such as bacteria transformed with recombinant bacteriophage DNA, plasmid DNA or cosmid DNA expression vectors containing the AGRP-1 coding sequence; yeast transformed with recombinant yeast expression vectors containing the AGRP-1 coding sequence; insect cell systems infected with recombinant virus expression vectors (e.g., Baculovirus) containing the AGRP-1 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the AGRP-1 coding sequence; or animal cell systems infected with recombinant virus expression vectors (e.g., Adenovirus, Vaccinia virus) containing the AGRP-1 coding sequence.

The expression elements of these vectors vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters (for example including but not limited to HSP70); the promoter for the small subunit of RUBISCO (small subunit of ribulose-1,5- bisphosphate carboxylase); the promoter for the chlorophyll a/b binding protein (the light harvesting chlorophyll a/b binding proteins) or from plant viruses (e.g., the 35S RNA promoter of CaMV (cauliflower mosaic virus); the coat protein promoter of TMV (tobacco mosaic virus)) may be used; when cloning in mammalian cell systems, promoters derived from the genome of mammalian cells (e.g., metallothionein promoter) or from mammalian viruses (e.g., the Adenovirus late promoter; the vaccinia virus 7.5K promoter) may be used. Promoters produced by recombinant DNA or synthetic techniques may also be used to provide for transcription of the inserted AGRP-1 coding sequence.

In bacterial systems a number of expression vectors may be advantageously selected depending upon the use intended for the AGRP-1 expressed. For example, when large quantities of AGRP-1 are to be produced, vectors which direct the expression of high levels of protein products that are readily purified may be desirable. Such vectors include, but are not limited to, the E. coli expression vector pUR278 (Ruther et al., EMBO J. 2:1791 (1983) incorporated herein by reference in it's entirety.), in which the AGRP-1 coding sequence may be ligated into the vector in frame with the lac Z coding region so that a hybrid AGRP-1-lac Z protein is produced; pIN vectors (Inouye & Inouye, Nucleic acids Res. 13:3101–3109 (1985); Van Heeke & Schuster, J. Biol. Chem. 264:5503–5509 (1989); incorporated herein by reference in their entirety).

In yeast, a number of vectors containing constitutive or inducible promoters may be used. For a review see, Current Protocols in Molecular Biology, Vol. 2, Ed. Ausubel et al., Greene Publish. Assoc. & Wiley Interscience, Ch. 13 (1988); Grant et al., Expression and Secretion Vectors for Yeast, in Methods in Enzymology, Eds. Wu & Grossman, 31987, Acad. Press, N.Y., Vol. 153, pp. 516–544 (1987); Glover, DNA Cloning, Vol. II, IRL Press, Wash., D.C., Ch. 3 (1986); and Bitter, Heterologous Gene Expression in Yeast, Methods in Enzymology, Eds. Berger & Kimmel, Acad. Press, N.Y., Vol. 152, pp. 673–684 (1987); and The Molecular Biology of the Yeast Saccharomyces, Eds. Strathern et al., Cold Spring Harbor Press, Vols. I and II (1982) all incorporated herein by reference in their entirety).

The AGRP-1 sequence may be cloned behind either a constitutive yeast promoter such as ADH or LEU2 or an inducible promoter such as GAL (Cloning in Yeast, Chpt. 3, R. Rothstein In: DNA Cloning Vol.11, A Practical Approach, Ed. D. M. Glover, IRL Press, Wash., D.C. (1986) incorporated herein by reference in its entirety). Constructs may contain the 5' and 3' non-translated regions of the corresponding to a yeast gene. YEp plasmids transform at high efficiency and the plasmids are extremely stable. Alternatively, vectors may be used which promote integration of foreign DNA sequences into the yeast chromosome.

In cases where plant expression vectors are used, the expression of the AGRP-1 coding sequence may be driven by any of a number of promoters. For example, viral promoters such as the 35S RNA and 19S RNA promoters of CaMV (Brisson et al., Nature 310:511–514 (1984) incorporated herein by reference in its entirety), or the coat protein promoter of TMV (Takamatsu et al., EMBO J. 6:307–311 (1987) incorporated herein by reference in its entirety) may be used; alternatively, plant promoters such as the small subunit of RUBISCO (Coruzzi et al., EMBO J. 3:1671–1680 (1984); Broglie et al., Science 224:838–843 (1984) all incorporated herein by reference in their entirety); or heat shock promoters, e.g., soybean hsp17.5-E or hsp17.3-B (Gurley et al. Mol. Cell. Biol. 6:559–565 (1986) incorporated herein by reference in its entirety) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach,, Methods for Plant Molecular Biology, Academic Press, N.Y., Section VIII, pp. 421–463 (1988); and Grierson & Corey, Plant Molecular Biology, 2d Ed., Blackie, London, Ch. 7–9 (1988) all incorporated herein by reference in their entirety.

An alternative expression system which could be used to express AGRP-1 is an insect system. In one such system, Autographa californica nuclear polyhedrosis virus (AcNPV) is used as a vector to express foreign genes. The virus grows in Spodoptera frugiperda cells. The AGRP-1 coding sequence may be cloned into non-essential regions (for example the polyhedrin gene) of the virus and placed under control of an AcNPV promoter (for example the polyhedrin promoter). Successful insertion of the AGRP-1 coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed. (See Smith et al., J. Viol. 46:584 (1983); U.S. Pat. No. 4,215,051 to Smith both incorporated herein by reference in their entirety).

In cases where an adenovirus is used as an expression vector, the AGRP-1 coding sequence may be ligated to an adenovirus transcription/translation control complex, e.g., the late promoter and tripartite leader sequence. This chimeric gene may then be inserted in the Adenovirus genome by in vitro or in vivo recombination. Insertion in a non-essential region of the viral genome (e.g., region E1 or E3) will result in a recombinant virus that is viable and capable of expressing AGRP-1 in infected hosts. (E.g., See Logan & Shenk, Proc. Natl. Acad. Sci. (USA) 81:3655–3659 (1984) incorporated herein by reference in its entirety). Alternatively, the Vaccinia 7.5K promoter may be used. (E.g., see Mackett et al., Proc. Natl. Acad. Sci. (USA) 79:7415–7419 (1982); Mackett et al., J. Virol. 49:857–864 (1984); Panicali et al., Proc. Natl. Acad. Sci. 79:4927–4931 (1982) all incorporated herein by reference in their entirety).

Specific initiation signals may also be required for efficient translation of inserted AGRP-1 coding sequences. These signals include the ATG initiation codon and adjacent sequences. In cases where the entire AGRP-1 coding sequence, including its own initiation codon and adjacent sequences, are inserted into the appropriate expression vectors, no additional translational control signals may be needed. However, in cases where only short ALA-GLN coding sequences (see items 1–4) are inserted, exogenous translational control signals, including the ATG initiation codon, [ALA-GLN, ALA-GLN-GLN] coding sequence are inserted to ensure translation of the entire insert.

These exogenous translational control signals and initiation codons can be of a variety of origins, both natural and synthetic. The efficiency of expression may be enhanced by the inclusion of appropriate transcription enhancer elements, transcription terminators, etc. (see Bitter et al., Methods in Enzymol. 153:516–544 (1987) incorporated herein by reference in its entirety).

In addition, a host cell strain may be chosen which modulates the expression of the inserted sequences, or modifies and processes the gene product in the specific fashion desired. Expression driven by certain promoters can be elevated in the presence of certain inducers, (e.g., zinc and cadmium ions for metallothionein promoters). Therefore, expression of the AGRP-1 may be controlled. This is important if the protein product of the cloned foreign gene is lethal to host cells. Furthermore, modifications (e.g., glycosylation) and processing (e.g., cleavage) of ALA-GLN/AGRP-1 protein products may be important for the function/stability of the protein. Different host cells have characteristic and specific mechanisms for the post-translational processing and modification of proteins. Appropriate cells lines or host systems can be chosen to ensure the correct expression.

EXAMPLE 11

Identification of Transfectants or Transformants Expressing AGRP-1 and Related Proteins The host cells which contain the AGRP-1 coding sequence and which express the biologically active AGRP-1 may be identified by one of several general approaches: (a) DNA-DNA hybridization; (b) the presence or absence of "marker" gene functions; (c) assessing the level of transcription as measured by the expression of AGRP-1 mRNA transcripts in the host cell; and (d) detection of the AGRP-1 product as measured by immunoassay or by its biological activity.

It will therefore be readily understood by those persons skilled in the art that the present invention is susceptible to broad utility and application. Many embodiments and adaptations of the present invention other than those herein described, as well as many variations, modifications and equivalent arrangements, will be apparent from or reasonably suggested by the present invention and foregoing description thereof, without departing from the substance or scope of the invention.

Accordingly, while the present invention has been described here in detail in relation to its preferred embodiment, it is to be understood that this disclosure is only illustrative and exemplary of the present invention and is made merely for the purposes of providing full and enabling disclosure of the invention. The foregoing disclosure is not intended to be construed or to limit the present invention or otherwise to exclude any other such embodiments, adaptations, variations, modifications and equivalent arrangements, the present invention being limited by the claims and the equivalents thereof.

What is claimed is:

1. An isolated nucleic acid sequence comprising a coding region that encodes for a glutamine rich peptide, said peptide consisting of the sequence MET(ALA-GLN)$_n$, -(protease cleavage site)-(ALA-GLN)$_n$ wherein n is a number ranging from 1 to 20.

2. The nucleic acid sequence of claim 1 further comprising a second sequence operably linked to said coding sequence, said second sequence encoding an intracellular, intercellular or secretory targeting signal.

3. The nucleic acid sequence of claim 1 wherein the protease cleavage sites are selected from the group consisting of trypsin, chemotrypsin, Factor Xa and TEV.

4. The nucleic acid sequence of claim 1 wherein the coding sequence is operably linked to an inducible or developmentally regulated promoter.

5. A transgenic host cell comprising the nucleic acid sequence of claim 1.

6. The host cell of claim 5 wherein the nucleic acid sequence further comprises a second sequence operably linked to said coding sequence, said second sequence encoding an intracellular, intercellular or secretory targeting signal.

7. The host cell of claim 5 wherein the host cell is a photosynthetic eukaryotic cell.

* * * * *

SEQUENCE LISTING

```
<160> NUMBER OF SEQ ID NOS: 13

<210> SEQ ID NO 1
<211> LENGTH: 53
<212> TYPE: PRT
<213> ORGANISM: Artificial Sequence
<220> FEATURE:
<223> OTHER INFORMATION: Glutamine rich peptide AGRP-1 as depicted in
      Figure 1.

<400> SEQUENCE: 1

Met Ala Leu Gln Gln Ala Gln Gln Ala Gln Gln Lys Val Gln Gln Asp
1               5                   10                  15

Ile Gln Gln Pro Ala Gln Gln Ala Gln Gln Gly Gln Gln Val Gln Gln
            20                  25                  30

Ala Gln Gln Asp Ile Gln Gln Thr Ala Gln Gln Ala Gln Gln Ile Gln
        35                  40                  45

Gln Arg Gln Gln Lys
    50

<210> SEQ ID NO 2
<211> LENGTH: 48
<212> TYPE: DNA
<213> ORGANISM: Artificial Sequence
<220> FEATURE:
<223> OTHER INFORMATION: Oligo 1 of Figure 1.

<400> SEQUENCE: 2
atggctcttc aacaggcaca gcaggctcaa cagaaacttc agcaggat                48

<210> SEQ ID NO 3
<211> LENGTH: 51
<212> TYPE: DNA
<213> ORGANISM: Artificial Sequence
<220> FEATURE:
<223> OTHER INFORMATION: Oligo 2 of Figure 1.
```

```
<400> SEQUENCE: 3
cgagaagttg tccgtgtcgt ccgagttgtc tttgaagtcg tcctataggt c           51

<210> SEQ ID NO 4
<211> LENGTH: 60
<212> TYPE: DNA
<213> ORGANISM: Artificial Sequence
<220> FEATURE:
<223> OTHER INFORMATION: Oligo 3 of Figure 1.

<400> SEQUENCE: 4
atccagcaac ccgctcagca ggctcaacag ggtcaacagg tgcagcaggc tcaacaggat   60

<210> SEQ ID NO 5
<211> LENGTH: 60
<212> TYPE: DNA
<213> ORGANISM: Artificial Sequence
<220> FEATURE:
<223> OTHER INFORMATION: Oligo 4 of Figure 5.

<400> SEQUENCE: 5
gttgggccag tcgaccgagt tgtcccagtt gtccacgtcg tccgagttgt cctataggtc   60

<210> SEQ ID NO 6
<211> LENGTH: 64
<212> TYPE: DNA
<213> ORGANISM: Artificial Sequence
<220> FEATURE:
<223> OTHER INFORMATION: Oligo 5 of Figure 1.

<400> SEQUENCE: 6
atccagcaaa ctgctcagca ggctcaacag atacagcagc gtcaacagaa ataggatccg   60
agct                                                               64

<210> SEQ ID NO 7
<211> LENGTH: 54
<212> TYPE: DNA
<213> ORGANISM: Artificial Sequence
<220> FEATURE:
<223> OTHER INFORMATION: Oligo 6 of Figure 1.

<400> SEQUENCE: 7
gtttgacgag tcgtccgagt tgactatgtc gtcgcagttg tctttatcct aggc         54

<210> SEQ ID NO 8
<211> LENGTH: 8
<212> TYPE: PRT
<213> ORGANISM: Artificial Sequence
<220> FEATURE:
<223> OTHER INFORMATION: Representative peptide based on Ala-Gln
      dipeptide repeat.

<400> SEQUENCE: 8

Ala Gln Ala Gln Ala Gln Ala Gln
1               5

<210> SEQ ID NO 9
<211> LENGTH: 9
<212> TYPE: PRT
<213> ORGANISM: Artificial Sequence
<220> FEATURE:
<223> OTHER INFORMATION: Representative peptide based on Ala-Gln
      dipeptide repeat with starting methionine residue
```

```
<400> SEQUENCE: 9

Met Ala Gln Ala Gln Ala Gln Ala Gln
1               5

<210> SEQ ID NO 10
<211> LENGTH: 12
<212> TYPE: PRT
<213> ORGANISM: Artificial Sequence
<220> FEATURE:
<223> OTHER INFORMATION: Representative peptide based on Ala-Gln-Gln
      tripeptide repeat.

<400> SEQUENCE: 10

Ala Gln Gln Ala Gln Gln Ala Gln Gln Ala Gln Gln
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Representative peptide based on Ala-Gln-Gln-Gln
      tetrapeptide repeat

<400> SEQUENCE: 11

Ala Gln Gln Gln Ala Gln Gln Gln Ala Gln Gln Gln
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Representative peptide based on Ala-Gln-Gln
      tripeptide repeat with starting methionine residue

<400> SEQUENCE: 12

Met Ala Gln Gln Ala Gln Gln Ala Gln Gln Ala Gln Gln
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Representative peptide based on Ala-Gln-Gln-Gln
      tetrapeptide repeat with starting methionine residue

<400> SEQUENCE: 13

Met Ala Gln Gln Gln Ala Gln Gln Gln Ala Gln Gln Gln
1               5                   10
```